United States Patent [19]

Sifniades et al.

[11] 3,988,320

[45] *Oct. 26, 1976

[54] SINGLE STAGE RESOLUTION/RACEMIZATION OF α-AMINO-ε-CAPROLACTAM

[75] Inventors: Stylianos Sifniades, Madison; William J. Boyle, Jr., Warren; Jan F. Van Peppen, Chester, all of N.J.

[73] Assignee: Allied Chemical Corporation, Morris Township, N.J.

[ * ] Notice: The portion of the term of this patent subsequent to Mar. 2, 1993, has been disclaimed.

[22] Filed: Apr. 7, 1975

[21] Appl. No.: 565,911

Related U.S. Application Data

[63] Continuation-in-part of Ser. No. 484,529, July 1, 1974, Pat. No. 3,941,776.

[52] U.S. Cl. .................. 260/239.3 R; 260/293.86; 260/326.5 FL
[51] Int. Cl.$^2$.......................................... C07D 223/08
[58] Field of Search ............... 260/239.3 R, 293.86, 260/326.5 FL

[56] References Cited
UNITED STATES PATENTS

| | | | |
|---|---|---|---|
| 3,024,231 | 3/1962 | Scherrer | 260/239.3 R |
| 3,105,067 | 9/1963 | Nelemans et al. | 260/239.3 R |
| 3,275,619 | 9/1966 | Brenner et al. | 260/239.3 R |
| 3,542,766 | 11/1970 | Ohnogi et al. | 260/239.3 R |
| 3,591,579 | 7/1971 | Shibahara et al. | 260/239.3 R |
| 3,658,811 | 4/1972 | Tanaka et al. | 260/239.3 R |
| 3,692,775 | 9/1972 | Kubanek et al. | 260/239.3 R |
| 3,824,231 | 7/1974 | Kubanek et al. | 260/239.3 R |
| 3,842,073 | 10/1974 | Fuhrmann et al. | 260/239.3 R |

*Primary Examiner*—Henry R. Jiles
*Assistant Examiner*—Robert T. Bond
*Attorney, Agent, or Firm*—Arthur J. Plantamura; Roger H. Criss

[57] ABSTRACT

Resolution of α-amino-ε-caprolactam with simultaneous racemization of the undesired D-α-amino-ε-caprolactam enantiomer is effected by forming a coordinately saturated α-amino-ε-caprolactam complex with $NiCl_2$, preferably crystallizing the L-α-amino-ε-caprolactam complex in the presence of fine seed crystals of L-α-amino-ε-caprolactam complex of $NiCl_2$ and catalytic amounts of a strong base selected from the alkoxides or hydroxides of Ni(II) and recovering L-α-amino-ε-caprolactam hydrochloride from the crystalline product.

12 Claims, 1 Drawing Figure

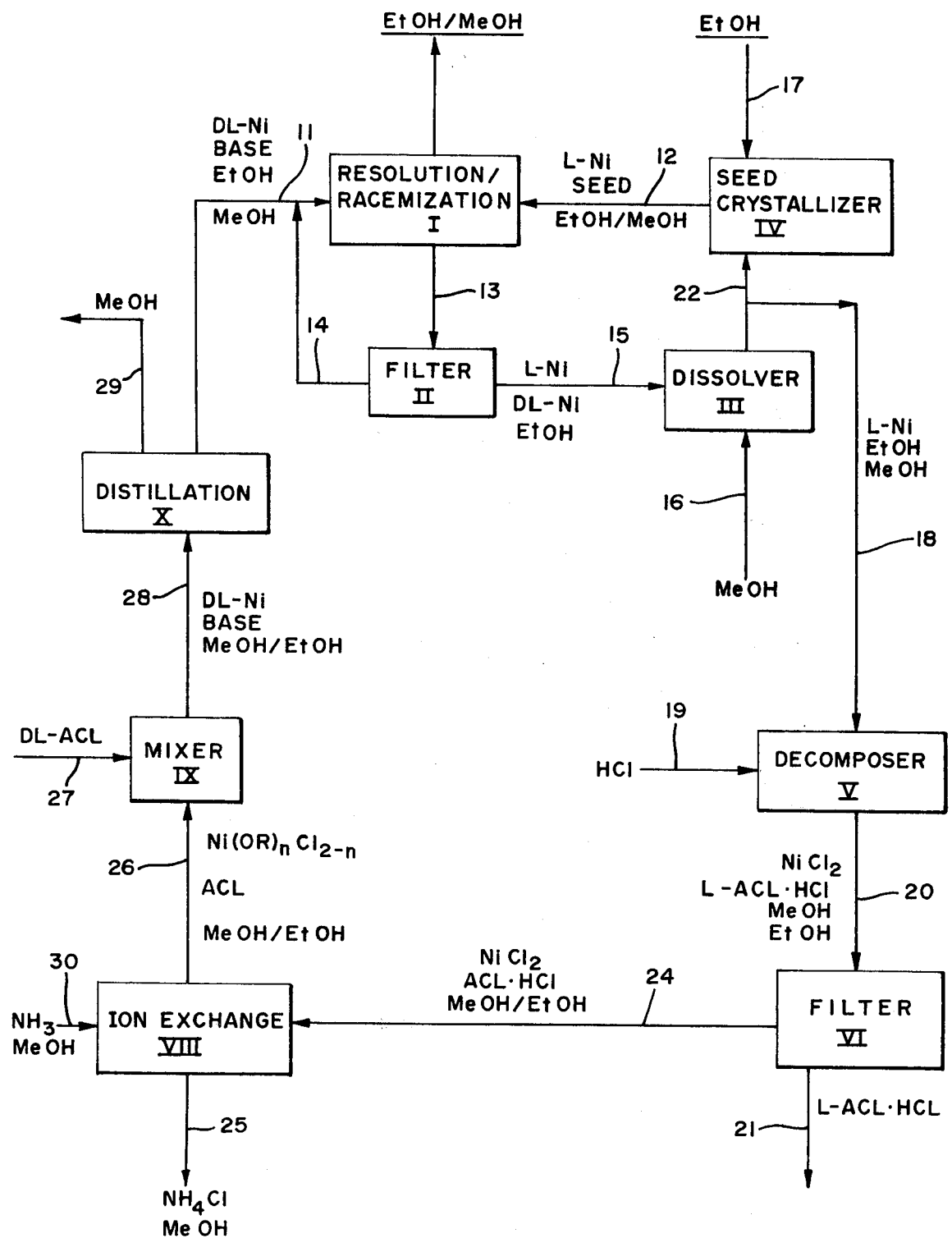

SINGLE STAGE RESOLUTION/RACEMIZATION OF α-AMINO-ε-CAPROLACTAM

This is a continuation-in-part of application Ser. No. 484,529 filed on July 1, 1974 now U.S. Pat. No. 3,941,776.

BACKGROUND OF THE INVENTION

1. Field of the Invention

The invention in a preferred embodiment relates to a simultaneous, one-stage resolution/racemization procedure for α-amino-ε-caprolactam

2. Brief Description of the Prior Art

Often one enantiomer of a compound having D- and L-forms is preferred over the other enantiomer of that compound. For example, lysine, an essential amino acid, exists in both D- and L-forms; however, only L-lysine possesses nutritional value. Although many synthetic methods for the production of lysine have been proposed, all non-biological methods have entailed preparation of either D,L-lysine or D,L-racemic modification of a lysine precursor such as D,L-lysine amide or D,L-α-amino-ε-caprolactam. If used in this racemic form, thee precursors would lead to the production of D,L-lysine or salt thereof. Such a mixture might conceivably be used without separation of the non-nutritional D-isomer but such a procedure would result in considerable waste. It is therefore advantageous to separate or resolve the two enantiomers to recover the desired enantiomer and then to racemize the nonnutritional or useless D-enantiomer to form additional D,L-racemic mixture from which the desired L-enantiomer is again recovered, with the procedure being repeated as often as desired. In accordance with a procedure of this kind, essentially all the D-enantiomer is in course transformed into the desired L-form.

SUMMARY OF THE INVENTION

We have discovered that solutions of α-amino-ε-caprolactam (ACL) can be rapidly racemized and simultaneously resolved by preferential crystallization of the complex of the L-isomer with nickel chloride in a highly improved and advantageous manner resulting in superior yield and optical purity by utilizing as catalyst a nickel alkoxide generated by an ion exchange resin.

A method for effecting resolution of D,L-α-amino-ε-caprolactam compounds is disclosed in our co-pending U.S. application, Ser. No. 484,529 filed July 1, 1974. A preferred embodiment of that application teaches a single stage process in which resolution of the desired enantiomer of a tris D,L-α-amino-ε-caprolactam complex with Ni(II), i.e., $Ni^{++}$, with simultaneous racemization of the undesired enantiomer is effected by contacting a supersaturated solution of the D,L-complex mixture with seed crystals of the desired enantiomer in the presence of a catalytic amount of a strong base and excess α-amino-ε-caprolactam free base. The function of α-amino-ε-caprolactam free base in excess of the amount required by the stoichiometry of formation of the metal complex is to ensure that no coodination sites are available on the metal ion by suppressing dissociation of the complex. Such coordination sites tend to complex the strong base which cannot then function as a racemization catalyst. Said application further discloses that strong bases suitable for use in said process include the alkali and alkaline earth metal salts and hydroxides thereof, such as potassium hydroxide, sodium hydroxide, and the like; carbonates such as sodium carbonate, calcium carbonate and the like; oxides, such as calcium oxide, magnesium oxide and the like; amides such as sodium amide, lithium amide and the like; alcoholates such as sodium ethoxide, potassium ethoxide and the like; and quaternary ammonium compounds such as tetrabutylammonium hydroxide, tetraisopropylammonium hydroxide and the like, as well as strongly basic anion exchange resins such as those of the quaternary ammonium type. In accordance with the present invention we have discovered that particularly well suited bases are hydroxides or alkoxides or basic salts of Ni(II) which is the metal ion of the complex of α-amino-ε-caprolactam used in the resolution/racemization reaction. Solutions of such hydroxides or alkoxides or basic salts can be conveniently prepared by treating an alcoholic or aqueous alcohol solution of a salt of the metal ion with any of a variety of commercially available strongly basic ion exchange resins of the quaternary ammonium type, e.g. ANGA-542 or Amberlite IR 400 or weakly basic ion exchange resins of tertiary amine type, e.g. Amberlite IR 45, Dowex 21K, etc. The amount of base employed is not critical provided that sufficient base is present to result in the racemization of α-amino-ε-caprolactam with a rate constant higher than 0.001 $min.^{-1}$. Generally from about 1 to about 100 mol percent of the base may be used although preferably about 5 to about 50 mol percent is used based on the metal ion.

BRIEF DESCRIPTION OF THE DRAWING

The flowsheet is illustrative of a continuous single stage process in which the α-amino-ε-caprolactam nickel chloride complex is racemized and resolved simultaneously according to a preferred embodiment of the invention.

DESCRIPTION OF THE PREFERRED EMBODIMENTS

A preferred embodiment of the present invention is the use of hydroxides or alkoxides or basic salts of nickel(II) as catalysts in the single stage resolution/racemization of α-amino-ε-caprolactam nickel(II) complex. In particular, use of nickel(II) compounds of the general formula $Ni(OR)_nCl_{2-n}$ in the single stage resolution/racemization of the complex of α-amino-ε-caprolactam with $NiCl_2$ of formula $(ACL)_3NiCl_2$ offers the unexpected advantage of significantly improving the optical purity of the crystals produced. Other advantages will become evident in the description of a continuous process described hereinbelow. In the above formula, R is hydrogen or a $C_1$ to $C_4$ alkyl radical, preferably R is methyl or ethyl; n is a number from 0.01 to 2; and ACL is α-amino-ε-caprolactam. It appears that the following theory explains the improved optical purity obtained during the resolution/racemization of $(ACL)_3NiCl_2$ when said basic salts are used as racemization catalyst. Use of other bases, such as NaOH, KOH, etc., results in the formation of insoluble chlorides, e.g. NaCl or KCl. These insoluble materials interface with the resolution process by providing nonselective sites for crystallization. The basic salts of $Ni^{++}$ do not present this problem, because $Ni^{++}$ is a normal component of the resolution/racemization system and does not form precipitates under the reaction conditions. It is not necessary to isolate these basic salts prior to use in the resolution/racemization process. Solutions of the salts can be prepared by treating substantially anhydrous solutions of $NiCl_2$ in a $C_1$ to $C_4$ alcohol with an alkali or alkaline earth metal hydroxide or alkoxide and filtering off the precipitated alkali metal or alkaline earth metal chloride which is formed. Another way of forming $Ni(OR)_nCl_{2-n}$ solutions is to treat said $NiCl_2$ solutions with a strongly basic ion exchange resin of the quaternary ammonium type such as the commercially available resins ANGA-542 or Amberlite IR 400.

A third, and preferred, way of forming $Ni(OR)_nCl_{2-n}$ solutions is to treat the $NiCl_2$ solutions with a weakly basic ion exchange resin of tertiary amine type such as the commercially available Amberlite IR 45, Dowex 21K, Dowex MWA-1, etc. One advantage of using weakly basic resins is that said resins can be regenerated after use by treatment with ammonia solutions, whereas strongly basic resins require the use of strong bases, e.g. sodium hydroxide, for regeneration. Since ammonia, on a mole basis, is much cheaper than any conceivable strong base, the economic advantage is apparent. Another advantage of using weakly basic resins is that the resin can be continuously operated under essentially anhydrous conditions.

The resolution/racemization process of the present invention is most advantageously carried out in substantially anhydrous media, because the presence of water causes, as an undesirable side reaction, partial hydrolysis of $\alpha$-amino-$\epsilon$-caprolactam to lysine. Advantageously, water in no case should exceed 5 percent and most preferably water should be present in amounts of less than 0.5 percent based on the solvent used. It is, therefore, desirable to obtain essentially anhydrous solution of $Ni(OR)_nCl_{2-n}$. In order to keep the presence of water to a minimum, it is necessary to use anhydrous ion exchange resins for the treatment of $NiCl_2$ solutions. A resin can be rendered anhydrous by extensive washing with anhydrous solvents, such as methanol. After the resin has been used for the treatment of $NiCl_2$ solutions, it must be regenerated to its basic form. Weakly basic resins can be easily regenerated under essentially anhydrous conditions, by using alcoholic, preferably methanolic, solutions of ammonia as regenerant. The by-product of the regeneration, ammonium chloride, is soluble in methanol and is easily removed from the system. The regenerated resin, therefore, remains substantially anhydrous and ready to be used for the treatment of a fresh solution of $NiCl_2$ without the necessity of repeating the extensive washing with alcohol. By way of comparison, if a strongly basic resin is used for the treatment of $NiCl_2$ solutions, it must be regenerated by sodium hydroxide. The sodium chloride formed as by-product during the regeneration is essentially insoluble in anhydrous alcohols, therefore, it is necessary to use water or aqueous alcohols in order to remove the by-product. This in turn necessitates renewed extensive washing with anhydrous alcohol in order to render the resin anhydrous. The economic advantage of using a weakly basic resin, therefore, is clear. Small amounts of $\alpha$-amino-$\epsilon$-caprolactam or $\alpha$-amino-$\epsilon$-caprolactam hydrochloride may be present during the formation of $Ni(OR)_nCl_{2-n}$ as they do not interfere with the process.

The solutions of basic salts of formula $Ni(OR)_nCl_{2-n}$ herein described may be used in the resolution/racemization of $\alpha$-amino-$\epsilon$-caprolactam either alone or in a mixture with $NiCl_2$. It will be understood that after admixture with $NiCl_2$ the solution still contains $Ni(OR)_nCl_{2-n}$, except that the value of n has been reduced to the extent that $NiCl_2$ has been added. Values of n ranging from 0.01 to about 1.00 may be used in the resolution/racemization process. The preferred values of n are from about 0.05 to about 0.50.

The basic nickel salts herein described do not function as racemization catalysts for $\alpha$-amino-$\epsilon$-caprolactam unless the nickel(II) ion is coordinately saturated. This can be accomplished by the addition of nickel(II) - coordinating compounds in excess to the amount required in order to satisfy the coordinating capacity of nickel(II). Such compounds are e.g. ammonia, ethylenediamine, sodium lysinate, 1,10-phenanthroline, etc. $\alpha$-Amino-$\epsilon$-caprolactam, when used in excess of 3 moles per nickel(II) ion, can render nickel(II) ion coordinately saturated and is preferred. While amounts ranging from 3 to 10 moles $\alpha$-amino-$\epsilon$-caprolactam per mole nickel(II) can be used, 3.5 to 7 moles are preferred.

A second preferred embodiment of the present invention is the use of very fine crystals of $(L-ACL)_3NiCl_2$ as seed crystals for the resolution/racemization and the means for producing and utilizing such crystals. We have found that it is possible to maintain a high crystallization rate and high optical purity of $(L-ACL)_3NiCl_2$ crystalline product with a minimum requirement for seed crystals if said seed crystals are essentially optically pure and of an average size below about 3 microns square, as viewed under a microscope. We have further found that very fine seed crystals (sized under 3 microns square) can be reliably produced by mixing a concentrated methanol solution of $(L-ACL)_3NiCl_2$ with a higher alcohol.

The alcohols of preference are ethanol and isopropanol. Mixing may be effected at any temperature between the freezing point and boiling point of mixture. Generally, the lower the temperature the smaller the size of the crystals formed. Temperatures close to the ambient are most economical and are preferred.

The alcohol used in causing crystallization of the L-$\alpha$-amino-$\epsilon$-caprolactam nickel chloride complex from the methanolic solution is generally incorporated in the crystal structure as one molecular of solvent of crystallization. For example, if ethanol is used, the crystals have the structure $(L-ACL)_3NiCl_2 \cdot EtOH$; if iso-propanol is used the structure is $(L-ACL)_3NiCl_2 \cdot i-PrOH$. The molecule of solvent of crystallization can be removed by heating the crystals at e.g. from 120° to 200° C., but removal is not necessary for the purposes of the resolution/racemization process. It is advantageous to conduct the resolution/racemization in essentially the same solvent as that included in the seed crystals. For example, if $(L-ACL)_3NiCl_2 \cdot EtOH$ seed crystals are used, ethanol, or ethanol/methanol mixture is used as solvent in the resolution/racemization. In the process of forming the seed crystals, D-$\alpha$-amino-$\epsilon$-caprolactam, if present in small amounts in the original solution, remains largely in solution in the form of $(D,L-ACL)_3NiCl_2$, therefore the crystals are of higher optical purity than the original solution. It is possible to separate the crystals from the solution by high speed centrifugation, hyperfiltration or similar costly techniques. We have found, however that such separation is not necessary and that the crystal slurry can be used as such as a source of seed crystals for the resolution/racemization process.

The preferred embodiments hereinabove described are particularly well suited for a continuous process of resolution/racemization of $\alpha$-amino-$\epsilon$-caprolactam via $(ACL)_3NiCl_2$. Thus, as it will be described in greater detail hereinbelow, alcoholic solutions of $NiCl_2$ containing small amounts of $\alpha$-amino-$\epsilon$-caprolactam hydrochloride are produced in such a process upon decomposition of $(L-ACL)_3NiCl_2$ with HCl. These solutions are treated with a weakly basic ion exchange resin which results in transformation of $\alpha$-amino-$\epsilon$-caprolactam hydrochloride to $\alpha$-amino-$\epsilon$-caprolactam and of $NiCl_2$ to $Ni(OR)_nCl_{2-n}$ which can be recycled as catalyst to the resolution/racemization reactor. The fine crystals of seed quality, which are the second preferred embodiment of the present invention, can also be conveniently produced in a continuous process. Thus, grown $(L-ACL)_3NiCl_2$ crystals from a resolution/racemization reactor are dissolved in methanol prior to decomposition by HCl. A small aliquot of the methanolic solution is treated with ethanol resulting in formation of a slurry of fine, optically enriched crystals of $(L-ACL)_3NiCl_2.EtOH$. This slurry is then recycled as a source of seed crystals to the resolution/racemization reactor. The temperature in the reactor is below 120° C., preferably between 40° and 95° C.

After resolution of $(L-ACL)_3NiCl_2$, L-$\alpha$-amino-$\epsilon$-caprolactam or a salt thereof can be recovered from the complex. Various conventional methods may be employed. A process which may be suitably used is one in which the metal complex which has crystallized out is dissolved or suspended in solvent, preferably a $C_1$ to $C_3$ alcohol, and treated with any strong non-oxidizing mineral acid, preferably hydrochloric, sulfuric or phosphoric. The acid effects decomposition of the complex and the simultaneous precipitation of the desired enantiomer of L-$\alpha$-amino-$\epsilon$-caprolactam as the acid salt. The decomposition can be effected at any temperature above about 0° C. This may conveniently be effected at ambient or slightly above ambient temperature.

The preferred acid for decomposition of the L-$\alpha$-amino-$\epsilon$-caprolactam metal complex is hydrochloric acid. As disclosed in U.S. Pat. No. 3,824,231, use of this acid provides the following advantage: Normally, the L-$\alpha$-amino-$\epsilon$-caprolactam metal complex obtained in the present resolution/racemization process contains small but definite amounts of D,L-$\alpha$-amino-$\epsilon$-caprolactam metal complex. When the decomposition of the complex is effected by hydrochloric acid, the $\alpha$-amino-$\epsilon$-caprolactam hydrochloride which crystallizes out is essentially optically pure, i.e. it is composed almost exclusively of L-$\alpha$-amino-$\epsilon$-caprolactam hydrochloride. The small amount of D,L-$\alpha$-amino-$\epsilon$-caprolactam hydrochloride, which is also produced during the decomposition, remains in solution. The solvents in which the decomposition is effected are $C_1$ to $C_3$ alkanols, used separately; or in mixture with each other or in a mixture with water. The solvent of preference is methanol.

Since the L-$\alpha$-amino-$\epsilon$-caprolactam is ordinarily further utilized in the form of its hydrochloride salt, this is the preferred form of this material. L-$\alpha$-amino-$\epsilon$-caprolactam hydrochloride can be hydrolyzed by known methods to afford L-lysine-hydrochloride salt.

A flowsheet illustrative of a continuous single stage resolution/racemization process is shown in the drawing. D,L-$\alpha$-amino-$\epsilon$-caprolactam nickel complex (represented in the drawing as DL-Ni) in methanol and ethanol originating in mixer IX and passing through distillation column X is fed at 11 into resolver/racemizer I along with make-up strong base catalyst. The base catalyst is produced by treatment of nickel chloride recycled liquor in ion exchanger VIII followed by mixing with D,L-ACL in mixer IX. The ion exchange treatment produces a basic $Ni^{++}$ salt which after admixture with ACL generates free alkoxide ions that are strongly basic. Additional amounts of strong base catalyst are provided by recycle stream 14. The level of the alkoxide ion in stream 11 is adjusted so that the level of alkoxide ions in reactor I is maintained from about 0.05 to about 0.50 moles per mole of $Ni^{++}$. Nickel complex seed crystals of the desired L-$\alpha$-amino-$\epsilon$-caprolactam 12 (represented in the drawing as L-Ni) are also introduced as a slurry in ethanol-methanol into reactor I. Ethanol and methanol are distilled and removed from reactor I. $(L-ACL)_3NiCl_2.EtOH$ crystallizes out in the presence of $(L-ACL)_3.NiCl_2.EtOH$ seed crystals while racemization of D-ACL occurs simultaneously in I. The reaction mixture is continuously withdrawn at 13 and filtered at II with the mother liquor 14 being added to recycled stream 11. Small amounts of alkoxide ions are removed from reactor I and not recycled thereto only to the extent of incomplete separation in filter II. Small amounts of alkoxide ions are also consumed in reactor I due to side reactions such as hydrolysis of $\alpha$-amino-$\epsilon$-caprolactam to lysine. The amount of alkoxide ions introduced through stream 11 should be sufficient only to supplant the amount lost and maintain the above noted, desired level in reactor I, i.e. from about 0.05 to about 0.50 moles per mole of $Ni^{++}$. The L-$\alpha$-amino-$\epsilon$-caprolactam nickel complex filter cake which is withdrawn from filter II at 15 is transferred to dissolver III wherein the cake is refluxed with methanol and dissolved. A portion 22 of the solution, approximately 2 to 25% of the stream from dissolver III, is introduced into seed crystallizer IV. At the same time ethanol 17 is introduced into crystallizer IV. In the crystallizer IV fine $(L-ACL)_3NiCl_2.EtOH$ crystals are formed. This ethanol-methanol crystal slurry is introduced at 12 as seed crystals to the reactor I. The balance 18 of the stream from dissolver III is introduced to the decomposer V where anhydrous HCl shown entering at 19 is introduced to effect decomposition of the metal complex. The contact with HCl decomposes the $(L-ACL)_3NiCl_2$ and precipitates optically pure L-ACL.HCl. Any lysine which may be present as impurity also crystallizes as lysine.HCl. The resulting stream 20 is filtered at VI and the crystalline L-ACL.HCl is collected at 21. The mother liquor removed at 24 comprises dissolved $NiCl_2$, a small amount of dissolved D,L-ACL.HCl and ethanol/methanol solvent. This mother liquor is neutralized by contacting with a weakly basic ion exchange resin in column VIII where the D,L-ACL.HCl is neutralized to the free base D,L-ACL and part of the $NiCl_2$ is transformed to basic nickel salt. The resin is regenerated to its basic form by a methanol solution of ammonia introduced at 30 which removes the chloride ions as a methano solution of $NH_4Cl$, as shown at 25. Small amounts of $Ni^{++}$ ion retained by the resin in column VIII are also removed in stream 25. Where desired, the regeneration of the ion exchange resin may be effected in two stages (not shown). In the first stage D,L-$\alpha$-amino-$\epsilon$-caprolactam in methanol solution is passed through column VIII. This operation removes $Ni^{++}$ ion preferentially to $Cl^-$. The eluent is introduced to mixer IX for further recycle. In the second stage the methanol solution of ammonia is passed through column VIII and the remaining $Cl^-$ ions are removed as $NH_4Cl$ and withdrawn at 25. The ethanol/methanol solution of ACL, $NiCl_2$, and nickel alkoxide via 26 is combined in mixer IX with feed D,L-ACL introduced at 27 to form a solution of D,L-α-amino-ε-caprolactam nickel complex and strong base catalyst. The thus produced solution introduced via line 28 is distilled at X to remove part of the methanol as shown at 29; the remaining stream 11 is recycled to I.

The continuous process hereinabove described can also be carried out by introducing iso-propanol, instead of ethanol, stream 17, into crystallizer IV. In that event, the seed crystals in the slurry withdrawn from crystallizer IV and the grown crystals withdrawn at filter II have the formula $(L-ACL)_3NiCl_2 \cdot i\text{-}PrOH$.

The invention will be further described by reference to the following Examples:

EXAMPLE 1

Semicontinuous Resolution/Racemization of $(ACL)_3NiCl_2$

For this experiment a reactor vessel consisting of a 150 ml 3-neck round-bottom flask equipped with a stopcock on the bottom for sampling the reaction mixture was employed. Samples were taken directly into interchangeable sintered-glass filter funnels where they were filtered under nitrogen pressure. Means were provided for washing the crystals on the filter. A tubing from the bottom of the filter automatically returned the mother liquid to the reaction vessel; a small port was provided for sampling the liquor in this tubing. The flask was equipped with a mechanical stirrer and a distallation head; a tube from a reservoir of make-up solution passed through the distillation head into the flask. The third neck of the flask was used for addition of the seed crystals. The flask was wrapped with heating tape for maintaining the desired temperature.

The initial charge was a 108 ml ethanol solution prepared from 55.7 ml (36 mmol) 0.646 M $NiCl_2 \cdot H_2O$ in ethanol, 23.1 g (180 mmol) D,L-ACL and 2.76 ml (5.4 mmol) 1.96 M NaOEt. Make-up solutions were prepared from 55.7 ml (36 mmol) 0.646 M $NiCl_2 \cdot H_2O$ ethanol solution, 14.3 g (111.6 mmol) D,L-ACL, 1.10 ml (2.16 mmol) 1.96 M NaOEt and sufficient ethanol to make a total of 100 ml. Two such make-up solutions were prepared.

The initial charge was introduced into the reactor and the solution brought to reflux, than 8.7 g (L-ACL)$_3$NiCl$_2$.EtOH seed crystals (formula weight 560) of 97% optical purity were added. The average size of the seed crystals was 6.8μ. After 10 minutes, addition of the first make-up was started and after addition was half complete the first sample (ca 25 ml) was filtered and 1.5 g seed crystals added. Sampling was repeated after each 25 ml addition from that point and was always accompanied by addition of 1.5 g seeds, of same size as above. The time of addition was adjusted to approximately 80 minutes per 100 ml. Throughout the operation ethanol was distilled off at a rate which was adjusted to maintain the volume of the reaction mixture approximately constant at 100 ml. Each sample was analyzed as follows: The crystalline cake obtained from filtration of the sample was dried in vacuo, weighed and optical rotation was determined in 1N HCl. The mother liquor was analyzed for Cl$^-$ ion and for optical rotation. From this analysis it was possible to determine the enantiomeric excess of D-ACL Ni$^{++}$ complex in solution. The data are presented in Table I. After 203 min. a total of 200 ml of make-up solution had been introduced to the reactor, besides the initial charge of 108 ml, and 7 samples had been withdrawn. At that point the volume of the reaction mixture was reduced to about 80 ml by evaporation of ethanol and the residue, after refluxing for about 30 more minutes, was filtered.

TLC analysis of this final mother liquor indicated approximately 1.5% lysine based on the total ACL charged in the

TABLE I

| | | Semicontinuous Resolutions/Racemization of $(D,L\text{-}ACL)_3NiCl_2{}^a$ | | | | | |
|---|---|---|---|---|---|---|---|
| | | Mother Liquor | | | Crop | | |
| Time | Feed, ml | Cl, meq. | [α]$^c$D | %D in excess | Wt,g | [α]$_D$ | Optical Selectivity$^d$ |
| 0 | 108, init charge | | | | | | |
| 10 min | 8.7g seed | | | | | | |
| 46 | 50$^b$ | 1.422/10ml | +1.32° | 3.9 | 3.04 | −22.4 | 96.5 |
| 67 | 75$^b$ | 1.312 | +1.19° | 3.5 | 4.99 | −21.6 | 93.5 |
| 87 | 100$^b$ | 1.312 | 0 | 0 | 3.62 | −21.6 | 93.5 |
| 110 | 125$^b$ | | | | 4.11 | −22.3 | 96.5 |
| 130 | 150$^b$ | 1.664 | +1.78° | 5.2 | 5.25 | −21.7 | 93.9 |
| 155 | 175$^b$ | | | | 5.08 | −22.0 | 95.2 |
| 172 | 200$^b$ | 1.278 | +1.34° | 3.9 | 4.38 | −21.7 | 93.9 |
| 203 | e | | | | | | |
| 238 | f | 2.31 | +0.68° | 2.0 | 28.0 | −21.9 | 94.8 |

$^a$Volume of reaction mixture approximately 100 ml.
$^b$Sample taken, 1.5 g seed added. Volume shown is cumulative exclusive of initial charge.
$^c$Based on 5ACL:2Cl−.
$^d$Based on [α]$_d$ = −23.1° for the seeds.
$^e$Volume of reaction mixture reduced to 80 ml by evaporation.
$^f$Reaction stoped; reaction mixture filtered.

course of the experiment. The combined crops of (L-ACL)$_3$NiCl$_2$.EtOH had a specific rotation of [α]$_D$=−21.6 (c=4, in 1N HCl) or 91% optical purity. Since the seeds used were 97% optically pure, the optical selectivity was 94%. The combined crops weighed 58.56 g

EXAMPLE 2

Preparation of Nickel Alkoxide Solution

A 2.5 cm by 65 cm column containing 131 g Amberlite IR-45 (a weakly basic resin, supplied by Rohm and Haas Co.) was thoroughly washed with methanol and converted to its basic form by treatment with a 2 molar solution of ammonia in methanol. The resin had total capacity for Cl$^-$ equal to 966 mequ. A 190 ml methanol solution, 1.07 M in NiCl$_2$, was slowly passed through the column at room temperature. The column was then washed with methanol. The combined eluent was titrated for Ni$^{++}$, Cl$^-$ and base. The base titration gave the content in total alkoxide ion. The solution was found to be 0.640 M in Ni$^{++}$, 1.055 M in Cl$^-$ and 0.225 M in alkoxide ion. The resin was subsequently regenerated to its basic form by treatment with a 2 molar solution of ammonia in methanol.

EXAMPLE 3

Semicontinuous Resolution/Racemization of $(ACL)_3NiCl_2.EtOH$ in the Presence of Nickel Alkoxide The apparatus and procedure described in example 1 was also used for this experiment. In order to prepare the initial charges and makeup solutions appropriate amounts of α-amino-ε-caprolactam and stock solutions A and B were mixed and diluted to the indicated volume with ethanol.

Solution A

Anhydrous $NiCl_2$, 100 g, was refluxed overnight with 1,500 ml of anhydrous ethanol. The mixture was cooled to room temperature and filtered under nitrogen. It was 0.386 M in $NiCl_2$.

Solution B

The preparation of this solution is described in Example 2.

The initial charge contained 162 mmoles of α-amino-ε-caprolactam, 36 mmoles of $Ni^{++}$ and 5.4 mmoles of total alkoxide ion in a volume of 120 ml. Each makeup solution contained 113.4 mmoles of α-amino-ε-caprolactam, 36 mmoles of $Ni^{++}$ and 1.08 mmoles of total alkoxide ion in a volume of 120 ml. Eight such makeup solutions were prepared.

The initial charge was introduced into the reactor and the solution was boiled. After about 20 ml had distilled off, 8 g of $(L-ACL)_3NiCl_2.EtOH$ seed crystals (formula weight 560) of 99% otical purity and of average size 4μ were added to the reactor. At the same time addition of the first makeup solution was started. Addition lasted for 3 hours. Every hour a 25 ml aliquot was filtered and 2 g of seed crystals were added. The level of the reaction mixture was maintained at about 110 ml by adjusting the rate of solvent distillation. The operation was continued for 27 hours at which time all the makeup solutions had been introduced to the apparatus. The total amount of seed crystals used was 62 g. During the operation the mother liquor from alternate filtrations was sampled and analyzed for optical activity and dissolved chloride ion. From these analyses the enantiomeric excess of D-ACL in solution was calculated to be 3–5% and the concentration of $(ACL)_3NiCl_2$ about 22%. The reaction mixture was refluxed for one more hour and then was filtered. The combined crystalline crops weighed 214 g (382 mmole (L-ACL)$_3$NiCl$_2$.EtOH) and had optical purity 97%. Since the optical purity of the seed crystals was 99%, this corresponds to 98% optical selectivity. Analysis of the final mother liquor indicated the presence of about 1 g of lysine by-product.

EXAMPLE 4

Preparation of Fine Seed Crystals of $(L-ACL)_3NiCl_2.EtOH$

A sample of 3.5 g of $(L-ACL)_3NiCl_2.EtOH$ (formula weight 560, 98% optically pure) was dissolved in 9 ml of refluxing methanol, then mixed with cold ethanol to total volume equal to 60 ml. After standing at room temperature for 1 hour, the mixture was shaken vigorously and a representative aliquot was viewed under a microscope at X850 magnification. Fine needle-shaped crystals were observed ranging in length from about 2 to about 20μ and in width from about 0.1 to 1.5μ. The average size of the crystals was estimated at less than 3μ square. Another aliquot was filtered, the crystals were washed with ethanol, dried in vacuo at 70° C. and analyzed for chloride ion and optical rotation. The chloride content corresponded to the formula (L-ACL)$_3$NiCl$_2$.EtOH. The optical rotation, $[\alpha]_D = -23.3$ (c=4, 1N HCl), corresponded to 100% optical purity.

EXAMPLE 5

Use of Fine Seed Crystals in the Resolution/Racemization of $(ACL)_3NiCl_2$

The apparatus described in Example 1 was used in this experiment. An initial charge, similar to the one described in Example 2, was placed in the apparatus and boiled. After about 20 ml of solvent has evaporated, a 15 ml aliquot of the fine crystal slurry described in Example 4 was introduced and evaporation was continued. When 20 ml of solvent had distilled, 120 ml of makeup solution, as described in Example 2, was added dropwise in the span of 3 hours. At the same time, small increments of the crystalline slurry described in Example 4 were introduced until a total volume of 51 ml of slurry had been used. During this time the volume of the reaction mixture was maintained at about 110 ml by simultaneous evaporation of solvent. After addition of the makeup solution and the seed slurry was completed, the mixture was refluxed for an additional period of 90 minutes, then it was filtered and the crystals were washed with ethanol and dried in vacuo at 70° C. The yield was 27.3 g of (L-ACL)$_3$NiCl$_2$.EtOH of 92% optical purity. Since the amount of (L-ACL)$_3$NiCl$_2$.EtOH used in making the seed crystals employed in the resolution was about 3 g, it is seen that the crop represents at least a nine-fold growth of the seed crystals.

EXAMPLE 6

Simultaneous Resolution/Racemization in Iso-Propanol/Methanol a. Preparation of (L-ACL)$_3$NiCl$_2$.i-PrOH Seed Crystals A sample of 3.98 g of (L-ACL)$_3$NiCl$_2$.EtOH was dissolved in 15 ml of refluxing methanol, then 25 ml of iso-propanol were added. The mixture was stirred for 1 minute at about 40° C. at which point it congealed due to deposition of extremely fine crystals. The crystals were filtered through a fine sintered glass filter, washed wit iso-propanol and dried in vacuo at 70° C. The equivalent weight was 286 g/Cl$^-$. Theoretical for (L-ACL)$_3$NiCl$_2$.i-PrOH is 287 g/Cl$^-$.

b. Resolution/Racemization

A methanol solution containing 5.76 g (45 mmole) of α-amino-ε-caprolactam, 10 mmole of Ni(II), 18.5 mmole Cl$^-$ and 1.5 mmole of total methoxide ion in total volume of 15 ml was prepared by mixing appropriate amounts of a methanol stock solution 1.30 M in NiCl$_2$, the nickel alkoxide solution described in Example 2, and crystalline α-amino-ε-caprolactam. To this solution was added a 25 ml portion of isopropanol and the mixture was heated to 65° C. Then 0.500 g of the (L-ACL)$_3$NiCl$_2$.i-PrOH seed crystals hereinabove described were added and the mixture was boiled for a total period of 3 hours. During this time, 7.5 ml of solvent was distilled and the pot temperature increased for 75° to 80.5° C. The grown (L-ACL)$_3$NiCl$_2$.i-PrOH crystals were separated by filtration, washed with i-PrOH and dried in vacuo at 70° C. The yield was 2.5 g and the optical purity 93%. Thwe enantiomeric excess of D-α-amino-ε-caprolactam in the mother liquor was about 4%.

It is to be understood that variations and modifications of the present invention will be apparent to those skilled in the art from the foregoing and such variations and changes may be made without departing from the scope of the invention. It is also to be understood that the scope of the invention is not to be interpreted as limited to the specific embodiment disclosed herein, but only in accordance with the appended claims when read in light of the foregoing disclosure.

We claim:

1. A process for effecting transformation of D,L-α-amino-ε-caprolactam complex with nickel(II) chloride to L-α-amino-ε-caprolactam complex with nickel(II) chloride which comprises:
   a. forming a supersaturated solution of said complex by mixing α-amino-ε-caprolactam with nickel(II) chloride and with nickel(II) hydroxide or nickel(II) alkoxide, in a solvent selected from $C_1$ $C_4$ alkanols and mixtures thereof, at a temperature below 120° C. and in proportions such that the molar ratio of α-amino-ε-caprolactam to nickel(II) is at least 3 and the molar ratio of hydroxide or alkoxide to nickel(II) is at least 0.01;
   b. containing said solution with seed crystals of L-α-amino-ε-caprolactam complex with nickel(II) chloride; and
   c. removing the grown crystals of said complex.

2. The process of claim 1 wherein the reaction temperature is in the range of about 40° to 95° C.

3. The process of claim 1 wherein the nickel(II) hydroxide or alkoxide is obtained by treating an alcoholic solution of $NiCl_2$ with a strongly basic or weakly basic ion exchange resin.

4. A process for effecting transformation of D,L-α-amino-ε-caprolactam to L-α-amino-ε-caprolactam hydrochloride comprising:
   a. admixing D,L-α-amino-ε-caprolactam with an ROH solution of $Ni(OR)_nCl_{2-n}$, wherein R is methyl, ethyl, or iso-propyl and $n$ has a value of from about 0.01 to about 1.00, in a molar ratio of α-amino-ε-caprolactam to Ni(II) of from at least 3:1 to about 10:1
   b. contacting the resulting solution with seed crystals of the formula $(L-ACL)_3NiCl_2.ROH$;
   c. removing the grown crystals of $(L-ACL)_3NiCl_2.ROH$; and
   d. decomposing said grown crystals by reaction with hydrogen chloride in ROH wherein R in each instance is as defined above, and removing the L-α-amino-ε-caprolactam hydrochloride formed.

5. The process of claim 1 wherein the seed crystals of L-α-amino-ε-caprolactam-nickel(II) chloride complex are prepared by mixing a methanolic solution of L-α-amino-ε-caprolactam-nickel(II) chloride complex with an alkanol selected from ethanol and isopropanol 6. A continuous process for effecting transformation of D,L-α-amino-ε-caprolactam to L-α-amino-ε-caprolactam hydrochloride comprising the steps of:
   a. generating a solution of basic nickel(II) salt by treating an alcohol solution of $NiCl_2$ with a weakly basic ion exchange resin;
   b. admixing said solution with at least three moles of D,L-α-amino-α-caprolactam per mol of nickel(II) thereby producing alkoxide ions;
   c. evaporating the resulting mixture from step (b) in the presence of seed crystals of $(L-ACL)_3NiCl_2.ROH$, where R is ethyl or iso-propyl, and continuously removing the grown resolved $(L-ACL)_3NiCl_2.ROH$ crystals;
   d. dissolving said grown crystals from step (c) in methanol;
   e. mixing from about 2 to about 25% of the resulting solution from step (d) with ethanol or iso-propanol and introducing the resulting slurry of fine $(L-ACL)_3NiCl_2.ROH$ crystals as seed to step (c); and
   f. reacting the balance of the solution from step (d) with HCl, removing the L-ACL-HCl crystals produced and recycling the resulting mother liquor to step (a).

7. The process of claim 6 wherein the molar ratio of α-amino-ε-caprolactam to nickel(II) in step (c) is from 3.5 to 7.0.

8. The process of claim 6 wherein the molar ratio of alkoxide ion nickel(II) in step (c) is from 0.05 to 0.50.

9. The process of claim 6 wherein the alcohol of crystallization in step (c) and the alcohol employed in step (e) is ethanol.

10. The process of claim 6 wherein the alcohol of crystallization in step (c) and the alcohol employed in step (a) is isopropanol.

11. The process of claim 6 wherein the resin of step (a) after removal of the basic nickel(II) salt is regenerated with an alcohol solution of ammonia.

12. The process of claim 6 wherein after generation of the solution of basic Ni(II) salt in step (a), small amounts of Ni(II) are removed from the weakly basic ion exchange resin by treatment with an α-amino-ε-caprolactam alcohol solution and the resulting nickel-(II) containing solution of α-amino-ε-caprolactam is introduced to step (b).

* * * * *

UNITED STATES PATENT AND TRADEMARK OFFICE
CERTIFICATE OF CORRECTION

PATENT NO. : 3,988,320
DATED : October 26, 1976
INVENTOR(S) : Stylianos Sifniades, William J. Boyle, Jr. and Jan F. Van Peppen It is certified that error appears in the above-identified patent and that said Letters Patent are hereby corrected as shown below:

Col. 2, line 61 "interface" should be -- interfere --.

Col. 11, line 23 "$C_1C_4$" should be -- $C_1$ to $C_4$ --.

line 29 "containing" should be -- contacting --.

Col. 12, line 29 "L-ACL-HCl" should be -- L-ACL·HCl --.

line 36 after the word "ion" insert -- to --.

line 42 "(a)" should be -- (e) --.

Signed and Sealed this

Fifth Day of April 1977

[SEAL]

Attest:

RUTH C. MASON
Attesting Officer

C. MARSHALL DANN
Commissioner of Patents and Trademarks